(12) United States Patent
Venkatraman et al.

(10) Patent No.: US 8,716,410 B2
(45) Date of Patent: May 6, 2014

(54) BIODEGRADABLE THERMOPLASTIC ELASTOMERS

(75) Inventors: Subramanian Venkatraman, Singapore (SG); Marc Abadie, Singapore (SG); Leonardus Kresna Widjaja, Singapore (SG); Vitali Llpik, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 13/509,566

(22) PCT Filed: Nov. 15, 2010

(86) PCT No.: PCT/SG2010/000433
§ 371 (c)(1),
(2), (4) Date: Jul. 25, 2012

(87) PCT Pub. No.: WO2011/059408
PCT Pub. Date: May 19, 2011

(65) Prior Publication Data
US 2012/0283391 A1    Nov. 8, 2012

Related U.S. Application Data

(60) Provisional application No. 61/260,955, filed on Nov. 13, 2009.

(51) Int. Cl.
*C08G 63/02* (2006.01)
*C08G 64/00* (2006.01)

(52) U.S. Cl.
USPC ............................ 525/411; 424/422; 606/230

(58) Field of Classification Search
USPC ............................. 424/422; 525/411; 606/230
See application file for complete search history.

(56) References Cited

U.S. PATENT DOCUMENTS

| | | | |
|---|---|---|---|
| 5,531,998 A | 7/1996 | Mares et al. | |
| 6,048,947 A * | 4/2000 | Oberhoffner et al. | 525/411 |
| 6,616,941 B1 | 9/2003 | Seo et al. | |
| 7,192,437 B2 | 3/2007 | Shalaby | |
| 2003/0236319 A1 | 12/2003 | Yoon et al. | |
| 2008/0262105 A1 | 10/2008 | Ferruti et al. | |
| 2009/0004243 A1 | 1/2009 | Pacetti et al. | |
| 2010/0152831 A1 | 6/2010 | Guo et al. | |

FOREIGN PATENT DOCUMENTS

EP        2 096 130 A1       9/2009

OTHER PUBLICATIONS

Kuredux PGA Data Sheet.*
Merck, 821037 Polyethylene glycol 2000 [retrieved on Aug. 6, 2012], retrieved from the internet at http://www.merck-chemicals.com/polyethylene-glycol-2000/MDA_CHEM-821037/p_1P2b.s1LvaMAAAEWruEfVhT1>.

Albertsson et al., "Degradable high-molecular-weight random copolymers, based on ε-caprolactone and 1,5-dioxepan-2-one, with non-crystallizable units inserted in the crystalline structure," *Polymer* 36(5): 1009-1016, 1995.
Amsden, "Curable, biodegradable elastomers: emerging biomaterials for drug delivery and tissue engineering," *Soft Matter* 3: 1335-1348, 2007.
Andronova et al., "Resilient Bioresorbable Copolymers Based on Trimethylene Carbonate, L-Lactide, and 1,5-Dioxepan-2-one," *Biomacromolecules* 7(5): 1489-1495, 2006.
Grijpma et al., "High molecular weight copolymers of L-Lactide and ε-caprolactone as biodegradable elastomeric implant materials," *Polymer Bulletin* 25: 327-333, 1991.
Jia et al., "Synthesis and characterization of tercopolymers derived from ε-caprolactone, trimethylene carbonate, and lactide," *Polymers for Advanced Technologies* 19: 159-166, 2008.
Kim et al., "Preparation and Properties of Poly(L-lactide- block-poly(trimethylene carbonate) as Biodegradable Thermoplastic Elastomer," *Polymer Journal* 34(3): 203-208, 2002.
Kricheldorf et al., "ABA triblock copolymers of L-lactide and poly-(ethylene glycol)," *Makromol Chem* 194: 715-725, 1993.
Kricheldorf et al., "Biodegradable Multiblock Copolyesters Prepared from ε-Caprolactone, L-Lactide, and Trimethylene Carbonate by Means of Bismuth Hexanoate," *Macromolecules* 38(20): 8220-8226, 2005.
Matsuda et al., "Molecular Design of Photocurable Liquid Biodegradable Copolymers. 1. Synthesis and Photocuring Characteristics," *Macromolecules* 33(3): 795-800, 2000.
Mizutani et al., "Liquid, Phenylazide-End-Capped Copolymers of ε-Caprolactone and Trimethylene Carbonate: Preparation, Photocuring Characteristics, and Surface Layering," *Biomacromolecules* 3(4): 668-675, 2002.
Pêgo et al., "Copolymers of trimethylene carbonate and ε-caprolactone for porous nerve guides: Synthesis and properties," *J Biomater Sci Polymer Edn* 12(1): 35-53, 2001.
Qian et al., "Synthesis, characterization and degradation of ABA block copolymer of L-lactide and ε-caprolactone," *Polymer Degradation and Stability* 68: 423-429, 2000.
Van Der Mee et al., "Investigation of Lipase-Catalyzed Ring-Opening Polymerizations of Lactones with Various Ring Sizes: Kinetic Evaluation," *Macromolecules* 39(15): 5021-5027, 2006.
Wu, "Synthesis and Properties of Biodegradable Lactic/Glycolic Acid Polymers," in *Encyclopedic Handbook of Biomaterials and Bioengineering*, Wise, Ed., Marcel Dekker, New York, 1995, pp. 1015-1054.
Zhang et al., "Triblock Copolymers Based on 1,3-Trimethylene Carbonate and Lactide as Biodegradable Thermoplastic Elastomers," *Macromol Chem Phys* 205: 867-875, 2004.

* cited by examiner

*Primary Examiner* — Terressa Boykin
(74) *Attorney, Agent, or Firm* — Seed IP Law Group PLLC

(57) ABSTRACT

The present invention relates to a biodegradable thermoplastic elastomer having the general formula A-B-A wherein each A is an amorphous polymer having a glass transition temperature (Tg)>40° C. or a semi-crystalline polymer having a glass transition temperature (Tg) and/or melting temperature (Tm) >40° C.; B is a copolymer of -caprolactone (CL) and at least one additional monomer selected from the group consisting of L-lactic acid (LLA), trimethyl carbonate (TMC), and glycolic acid (GA), or B is different to A and is lactic-co-glycolic acid (LGA); and wherein the molar ratio of CL to the at least one additional monomer in the copolymer B is in the range between about 1:0.09 to about 1:1.

31 Claims, 4 Drawing Sheets

BIODEGRADABLE THERMOPLASTIC ELASTOMERS

CROSS-REFERENCE TO RELATED APPLICATIONS

The present application claims the benefit of priority of US provisional application "A novel biodegradable thermoplastic elastomer" being filed with the US Patent and Trademark Office on Nov. 13, 2009 and being assigned the official Ser. No. 61/260,955. The content of this application filed on Nov. 13, 2009 is incorporated herein in its entirety by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates to biodegradable thermoplastic elastomers, a method for their preparation and the use of such biodegradable thermoplastic elastomers.

BACKGROUND

Although thermoplastic elastomers (TPE) have been around for quite some time, intensive research for biodegradable TPE just started recently and there are not many commercial elastomeric biodegradable materials in the market today. Biodegradable TPE have the potential uses as implantable devices because of their controllable elasticity and the possibility of changing their chemistry and structure. They also have potential applications in the biomedical area, especially in the area of controlled drug delivery and tissue engineering.

Generally, biodegradable TPE are in the form of A-B-A triblock copolymers with B as the so-called "soft segment" and A as the so-called "hard segment". A-B-A triblock copolymers with ε-caprolactone (ε-CL or CL) as the B block and L-lactide (LA) as the A block have been done by Qian et al (Polymer Degradation and Stability 2000, 68(3), 423-429), but due to the crystallinity of ε-CL the triblock copolymers did not have any elasticity at all despite the good elongation results. Meanwhile, similar triblock copolymers but with trimethyl carbonate (TMC) as the B block have also been studied. With TMC being an amorphous middle block, the triblock copolymers were said to be elastic although no data was provided regarding their recovery properties. Random copolymers of ε-CL and TMC with interesting mechanical properties were synthesized, but not related to the thermoplastic elastomers synthesis. A-B-A triblock copolymers with ε-CL and TMC as amorphous central blocks and L-lactide as crystalline blocks have also been investigated by Kricheldorf and Rost (Macromolecules 2000, 33 (3), 795-800) but in order to get good mechanical properties, the triblock copolymers have to be transformed into multiblock copolymers by chain extension with 1,6-hexamethylenediisocyanate (HMDI), which toxicity is often questioned. Furthermore, only minimal mechanical properties testing were done to the triblock copolymers.

Therefore, there is a need to provide triblock copolymers having improved elastic properties as thermoplastic elastomers.

SUMMARY

In a first aspect, the present invention provides a biodegradable thermoplastic elastomer having the general formula

A-B-A wherein each A is an amorphous polymer having a glass transition temperature (Tg)>about 40° C. or a semi-crystalline polymer having a glass transition temperature (Tg) and/or melting temperature (Tm)>about 40° C.;

B is a copolymer of ε-caprolactone (CL) and at least one additional monomer selected from the group consisting of L-lactic acid (LLA), trimethyl carbonate (TMC), and glycolic acid (GA), or B is different to A and is lactic-co-glycolic acid (LGA); and wherein the molar ratio of CL to the at least one additional monomer in the copolymer B is in the range between about 1:0.09 to about 1:1.

In a second aspect, the present invention provides a medical device comprising the inventive biodegradable thermoplastic elastomer.

In a third aspect, the present invention provides a packaging material comprising the inventive biodegradable thermoplastic elastomer.

In a fourth aspect, the present invention provides a method for preparing a biodegradable thermoplastic elastomer comprising:

reacting a mixture of ε-caprolactone, at least one additional monomer, an initiator and tin-2-ethylhexanoate in an organic solvent in order to obtain (co)polymer B;
adding monomer A;
reacting the obtained mixture of (co)polymer B and monomer A;
precipitating the obtained polymer.

BRIEF DESCRIPTION OF THE DRAWINGS

The invention will be better understood with reference to the detailed description when considering in conjunction with the non-limiting examples and the accompanying drawings.

DETAILED DESCRIPTION OF THE INVENTION

Figure 1:
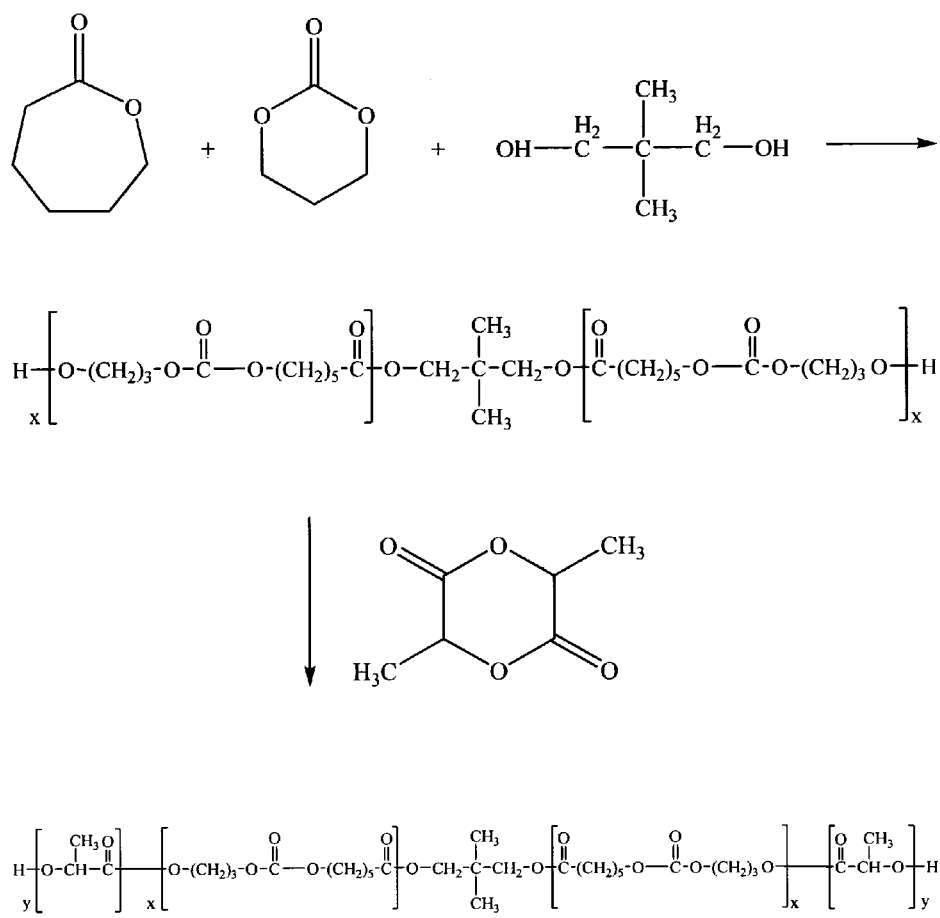
FIG. 1 illustrates an exemplary reaction scheme for the preparation of an inventive biodegradable thermoplastic elastomer.

In the following description non-limiting embodiments of the present invention will be explained.

According to the present invention, it has been surprisingly found that biodegradable thermoplastic elastomers can be obtained having improved mechanical properties, such as modulus, tensile strength and maximum strain. Generally speaking, the elastic properties of the inventive elastomers are improved over the properties of the elastomers of the prior art.

The biodegradable thermoplastic elastomer of the present invention is a triblock copolymer of the general formula A-B-A. In the general formula A is an amorphous polymer having a glass transition temperature (Tg)>about 40° C. or a semi-crystalline polymer having a glass transition temperature (Tg) and/or melting temperature (Tm)>about 40° C. "Amorphous polymer" according to the present invention is a polymer that is (totally) lacking positional order on the molecular scale, wherein a "semi-crystalline polymer" is a polymer that contains both crystalline and amorphous regions in the same polymer.

Polymer A may be considered as "end-block polymer" of the inventive biodegradable thermoplastic elastomer. It may act as the "hard" or anchoring segment that provides the physical crosslinks. Polymer A may have a glass transition temperature of >about 40° C. in case A is an amorphous polymer. For example, the glass transition temperature may be, but is not limited to, >about 42° C., >about 44° C., >about 46° C., >about 48° C., or >about 50° C. In case A is a semi-crystalline polymer, the polymer has a glass transition temperature of >about 40° C. and/or a melting temperature of >about 40° C. In one embodiment, the glass transition temperature may be, but is not limited to, >about 42° C., >about 44° C., >about 46° C., >about 48° C., or >about 50° C., whereas the melting temperature may be, but is not limited to, >about 42° C., >about 44° C., >about 46° C., >about 48° C., or >about 50° C. Any combination of the above-mentioned glass transition temperatures and melting temperatures is possible for the polymer of the present invention. In one embodiment, A is a semi-crystalline polymer having a glass transition temperature (Tg) or melting temperature (Tm)>about 40° C.

Generally, any polymer that fulfills the above requirements may be useful as polymer A in the present invention. In one embodiment, polymer A may be, but is not limited to, poly (lactic acid) (PLA), poly-L-lactic acid (PLLA), poly-DL-lactic acid (PDLLA), poly(glycolic acid) (PGA), poly(lactic-co-glycolic acid) (PLGA), and the like. In one embodiment, a combination of these polymers may be used, also in combination with other polymers not explicitly mentioned above and which may not alter the above described properties of the polymer. In one embodiment polymer A may be poly(lactic acid). It will clear to the skilled person that the polymers may be prepared from the respective monomers or mixtures of monomers.

Polymer A may be considered as block polymer having a segment length of at least about 10 units. This means that at least 10 monomeric units are polymerized to form polymer A. In one embodiment, the segment length may be, but is not limited to, at least about 15 units, such as at least about 20 units, at least about 30 units, at least about 40 units, at least about 50 units, at least about 100 units, or the like.

Polymer A may have a molecular weight of at least about 10.000 u. In one embodiment of the present invention the molecular weight of polymer A may be, but is not limited to, at least about 15.000 u, at least about 20.000 u, at least about 25.000 u, at least about 30.000 u, at least about 35.000 u, at least about 40.000 u or at least about 40.000 u.

B is the middle segment of the triblock elastomer A-B-A and may be called the "soft" segment. In one embodiment this segment is made to be amorphous. B may be poly(lactic-co-glycolic acid) (PLGA) being different to polymer A. Different in this respect means that A and B are not the same. In one embodiment amorphous LGA may be used for preparing B, for example in a 50:50 ratio with LA. In one embodiment, an additive, such as a plasticizer (see below) may additionally be added to the PLGA in order to adapt Tg. In one embodiment, B may be a copolymer of ε-caprolactone (CL) and at least one additional monomer. The additional monomer may be selected from any polymer which, in combination with CL, may be useful for the purpose of the present invention. For example, the additional monomer may be, but is not limited to, L-lactic acid (LLA), trimethyl carbonate (TMC), glycolic acid (GA), lactic-co-glycolic acid (LGA), mixtures thereof, and the like. In one embodiment B is a copolymer of the monomers CL and TMC. In one embodiment copolymer B may additionally contain further monomers to obtain a middle segment having the desired properties. For example, the crystallinity of the middle segment B may be adjusted. In one embodiment of the present invention the crystallinity may be, but is not limited to, <about 10%, <about 9%, <about 8%, <about 7%, <about 6%, <about 5%, and the like.

In one embodiment of the present invention B may have a glass transition temperature (Tg) of <about 40° C. For example, Tg of B may be, but is not limited to, <about 35° C., <about 30° C., <about 25° C., <about 20° C., <about 15° C., <about 10° C., <about 5° C., <about 0° C., or the like. In one embodiment, the glass transition temperature may be further adapted by introducing one or more additives as defined below. For example, in case B is PLGA a plasticizer, such as triethyl citrate, may be added to decrease Tg, if necessary. In one embodiment, B may have a segment length of at least about 50 units. This means that at least 50 monomeric starting units are polymerized to form B. In one embodiment, the segment length may be, but is not limited to, at least about 75 units, such as at least about 100 units, at least about 125 units, at least about 150 units, at least about 175 units, at least about 200 units, and the like.

B may have a molecular weight of at least about 20.000 u. In one embodiment of the present invention the molecular weight of B may be, but is not limited to, at least about 25.000 u, at least about 30.000 u, at least about 35.000 u, at least about 40.000 u, at least about 45.000 u, at least about 50.000 u, at least about 75.000 u, at least about 100.000 u, and the like. In one embodiment the mechanical properties of the elastomer may also depend on the molecular weight of B. For example, in case CL is used in an amount of >about 50% in the copolymer B, the molecular weight may be >about 40.000 u, such as >about 45.000 u, >about 47.500 u, >about 50.000 u, >about 55.000 u, >about 60.000 u, or the like.

The molar ratio of the monomers in B may influence the properties of the copolymer and thus the properties of the biodegradable thermoplastic elastomer. For example, depending on the molar ratio, modulus, tensile strength and maximum strain may be influenced. In one embodiment of the present invention the molar ratio of CL to the at least one additional monomer in B is in the range between about 1:0.09 to about 1:1. In one embodiment of the present invention the elastomer does not contain any 1,6-hexamethylene diisocyanate. In another embodiment of the present invention the molar ration of CL to the at least one additional monomer may be in the range of, but is not limited to, about 1:0.09 to about 1:0.99, about 1:0.09 to about 1:0.5, about 1:0.2 to about 1:0.4, or the like. In one embodiment, the molar ratio of CL:additional monomer may be, but is not limited to, about 1:0.09, about 1:0.1, about 1:0.15, about 1:0.20, about 1:0.25, about 1:0.30, about 1:0.35, about 1:0.40, about 1:0.45, about 1:0.50, about 1:0.55, about 1:0.60, about 1:0.65, about 1:0.70, about 1:0.75, about 1:0.80, about 1:0.85, about 1:0.90, about 1:0.95, about 1:0.99, about 1:1, and the like. In one embodiment the molar ratio CL:additional monomer is about 1:0.33 or about 1:0.11. In one embodiment, the mechanical properties, such as max. strain, may be particularly improved in case the molar ratio of CL is >50% in polymer B.

The biodegradable thermoplastic elastomer may have a molecular weight of at least about 35.000 u. For example, the molecular weight may be, but is not limited to, at least about 37.500 u, at least about 40.000 u, at least about 42.500 u, at least about 45.000 u, at least about 47.500 u, at least about 50.000 u, at least about 75.000 u, at least about 80.000 u, at least about 100.000 u, at least about 160.000 u, or the like. The molecular weight generally depends on the monomers/polymers used and on the specific reaction conditions used for preparing the biodegradable thermoplastic elastomer of the present invention. In one embodiment, the molecular weight of each A is about 10.000 u, about 20.000 u or about 40.000 u and the molecular weight of B is about 40.000 u or about 80.000 u. For example, the molecular weight of A may be about 10.000 u and the molecular weight of B may be 40.000 u, or the molecular weight of A may be about 10.000 u and the molecular weight of B may be 80.000 u, or the molecular weight of A may be about 20.000 u and the molecular weight of B may be 40.000 u, or the molecular weight of A may be about 20.000 u and the molecular weight of B may be 80.000 u, or the molecular weight of A may be about 40.000 u and the molecular weight of B may be 80.000 u.

The overall molar ratio of CL:additional monomer:polymer A may be between and including about 1:0.09:0.25 to about 1:1:1.35. In one embodiment the overall molar ratio may be between, but is not limited to, about 1:0.09:0.25 to about 1:0.99:1.35, such as between about 1:0.2:0.5 to about 1:0.30:0.85.

In addition to the above, in one embodiment of the present invention an additive may be added to the polymer A. An additive according to the present invention may be any compound that may influence the properties of polymer A. For example, by adding such an additive the crystallinity, degradation rate, glass transition temperature, melting temperature or the like may be altered, for example the crystallinity may be decreased. The additive may be, but is not limited to, a monomeric compound, a polymeric compound, a plasticizer such as triethyl citrate, a surfactant, a stabilizer, a cross-linking agent, a chain-transfer agent, and the like. Examples of monomeric compounds are, but not limited to, $\epsilon$-caprolactone, glycolic acid, and the like, wherein examples of polymeric compounds are, but not limited to, poly(caprolactone) (PCL), poly(glycolic acid) (PGA), and the like. In one embodiment the additive is CL. The additive may be added in an amount suitable to achieve the desired influence of the properties of polymer A. For example, the additive may be added in an amount of about 5 to about 35 wt.-%, such as about 10 to about 30 wt.-%. In one embodiment of the present invention the additive may be added in an amount of, but is not limited to, about 5 wt.-%, about 10 wt.-%, about 15 wt.-%, about 20 wt.-%, about 25 wt.-%, about 30 wt.-%, or about 35 wt.-%, and the like. The additive may be added before the preparation of polymer A, i.e. before the polymerization of the respective monomer, or may be added to the final polymer. For example, in case the additive is a monomeric compound, the monomer may be copolymerized with the monomers for the preparation of polymer A. In one embodiment of the present invention CL may be present in amount of >about 50%, such as >about 55%, >about 60%, >about 65%, >about 70% or >about 75% in copolymer B in case CL is also used as additive in polymer A. In one embodiment, B may also contain additional additives as described and defined above in order to influence the properties of the polymer. For example, a plasticizer may be added to adapt the glass transition temperature or the like.

Generally, the glass transition temperature Tg of the final elastomer may be the same as the glass transition temperature of A and B. For example, Tg of the final elastomer may be the sum of Tg of A and Tg of B or may be the mean value of Tg of A and Tg of B. In one embodiment Tg of the final elastomer may be different from Tg of A and/or Tg of B. For example, Tg of the final elastomer may be, but is not limited to, <about 50° C., <about 45° C., <about 40° C., <about 35° C., <about 30° C., <about 25° C., <about 20° C., <about 15° C., <about 10° C., <about 5° C., <about 0° C., and the like. In a further embodiment of the present invention Tg of the final elastomer may be, but is not limited to, >about 0° C., >about 10° C., >about 20° C., >about 30° C., >about 40° C., >about 50° C., and the like.

The biodegradable thermoplastic elastomer of the present invention may be prepared in a "one-pot-procedure". According to the inventive process, a mixture of $\epsilon$-caprolactone, at least one additional monomer, an initiator and tin-2-ethylhexanoate is reacted in an organic solvent in order to obtain copolymer B. To this copolymer B monomer A is added and the obtained mixture of copolymer B and monomer A is reacted. Finally, the obtained biodegradable thermoplastic monomer is precipitated.

In one embodiment of the present invention, lactic-co-glycolic acid (LGA) ist used instead of $\epsilon$-caprolactone and at least one additional monomer.

In one embodiment one or more additive as defined above may be added at any stage of the preparation process in order to alter the properties of A and/or B.

The at least one additional monomer may be selected from the group defined above. In one embodiment the at least one additional monomer is trimethyl carbonate (TMC).

The initiator is used to inter alia control the molecular weight of the synthesized polymer. Generally, the initiator may be chosen from any initiator which is used in the field of polymer chemistry. In one embodiment, the initiator may be a diol such as, but not limited to, ethylene glycol, 2,2-dimethyl-1,3-propandiol, butandiol, and the like.

The organic solvent used in the preparation of the copolymer B may be any solvent which is generally used in polymerization reactions. In one embodiment, the organic solvent may be, but is not limited to, toluene, benzene, tetrahydrofuran, mixtures thereof, and the like. The skilled person will be fully aware of the solvent being suitable for the respective reaction.

In the present invention, a catalyst may be used to influence the reaction. In one embodiment, the catalyst may be, but is not limited to, a homoleptic tin (II) complex, heteroleptic tin (IV) complex, a mixture thereof, and the like. For example, tin-2-ethylhexanoate may be used as catalyst. This catalyst is readily available, non-toxic and has been approved by the FDA as food additive.

The monomer A may be selected from the group consisting of lactic acid (LA), L-lactic acid (LLA), DL-lactic acid (DLLA), glycolic acid (GA) and lactic-co-glycolic acid (LGA). In one embodiment, the monomer A is lactic acid.

The final product is precipitated from the reaction mixture. Several precipitation methods may be used in the present invention, such as, but not limited to, temperature change, addition of one or more solvent(s), and the like. The solvent, which may be used to initiate precipitation, may be any solvent suitable for precipitating the polymer. For example, the solvent may be, but is not limited to, ethanol, hexane, diethyl ether, mixtures thereof, and the like.

The reaction for preparing copolymer B may be carried out as one-pot-procedure. All starting materials are mixed together, wherein the addition order is of no relevance. The mixture is refluxed for a time sufficient to polymerize all monomers present in the mixture. For example, the mixture may be refluxed for about 6 hours, about 12 hours, about 18 hours or about 24 hours. After adding monomer A to the obtained copolymer B, the resulting mixture is refluxed again for about 6 hours, about 12 hours, about 18 hours or about 24 hours.

The monomers used in the inventive preparation process are chosen in an amount and ratio as already explained above.

The target was to make the soft segment to be completely amorphous or at least having minimum cristallinity, thus giving the triblocks a large elongation. Then this soft segment would be coupled with the hard block made of polymer A, which would act as an anchor point to give the elastic property of the biodegradable thermoplastic elastomer.

The biodegradable thermoplastic elastomer of the present invention may be used for several applications. For example, it may be used as (part of) a medical device or packaging material.

The medical device may be an implantable device selected from stent, an occlude for patent foramen ovale (PF) or atrial septal defect (ASD) or patent ductus arteriosus (pda), a scaffold for tissue engineering, implant applications and surgical suture materials. For example, the stent may be a fully-degradable stent in the coronary, peripheral arteries, and in the trachea, biliary duct and ureter.

The packaging material may be, but is not limited to, a film, tape, cut, paper and cloth.

In the context of the present invention, the term "comprising" means including, but not limited to, whatever follows the word "comprising". Thus, use of the term "comprising" indicates that the listed elements are required or mandatory, but that other elements are optional and may or may not be present. The term "consisting of" means including, and limited to; whatever follows the phrase "consisting of". Thus, the phrase "consisting of" indicates that the listed elements are required or mandatory, and that no other elements may be present. The term "consisting essentially of" means including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to the skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject-matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

EXAMPLES

The following experimental examples are provided to further illustrate the present invention and are not intended to be limiting to the scope of the invention.

Materials

The monomers, $\epsilon$-caprolactone ($\epsilon$-CL) (99%) was obtained from Fluka, L-lactide was obtained from Sigma Aldrich, and trimethylene carbonate (TMC) was purchased from Boehringer Ingelheim. The initiator, 2,2-dimethyl-1,3-propanediol (purum, >99.0%) from Fluka and the catalyst, tin-(II)-2-ethylhexanoate (SnOct$_2$) from Sigma Aldrich were used as received. Toluene anhydrous (99.8%) was purchased from Sigma Aldrich and used as the polymerization solvent.

Measurement

Number average (Mn), weight average (Mw) molecular weights, and molecular weight distributions (Mw/Mn) were obtained by size exclusion chromatography (Shimadzu LC-20AD). Chloroform was used as eluent at a flow rate of 1.5 ml/min. Narrow polystyrene standards were used for calibration. All measurements were performed at 25° C.

Compositions of s-caprolactone, TMC, and L-lactide inside the polymer were observed by $^1$H NMR and $^{13}$C NMR spectroscopy taken on a Bruker 400 MHz Spectrometer using deuterated CDCl$_3$ as the solvent.

Glass transition temperatures ($T_g$) and melting temperatures ($T_m$) of purified polymers were measured by differential scanning calorimetry (DSC). Samples (5-10 mg) were analyzed at a heating rate of 10° C./min in a temperature range of −90 to 225° C. using TA Instruments Model Q10 DSC machine. All samples were scanned using two cycles heating and reported values were determined from the second scan.

Solutions of polymer in solvent (10% w/v) were cast on glass petri dishes. After drying under room temperature for 4 days followed by drying in a vacuum for 2 days, 0.2-0.3 mm thick films were obtained. From these films, specimens for mechanical testing were cut into standard dog-bone shaped samples. Tensile test was carried out using the INSTRON 5848 microtester according to ASTM D882-91 standards.

Example 1

Preparation of A-B-A- Triblock Copolymers

ABA triblock copolymers, where A is a PLLA hard segment and B is the soft segment made of random copolymer of PCL and PTMC were prepared by one-step living coordinated anionic ring-opening polymerization. The syntheses were done in a two necks round bottom flask (100 ml) equipped by thermometer, condenser and magnetic stirrer. The flask was purged by nitrogen, vacuumed twice and after that the flask was kept under the nitrogen atmosphere. A mixture of $\epsilon$-CL and TMC monomers were added to the toluene and then a certain amount of initiator was added according to the desired degree of polymerization, lastly Sn(Oct)$_2$ as catalyst was added to the mixture and the flask was immersed into silicone oil bath with temperature of 140° C. for 24 hours. After that, a defined quantity of L-lactide was added to the flask and the mixture was kept another 24 hours. Polymer was precipitated in methanol and dried under vacuum for 3 days. In FIG. 1 the general reaction scheme can be seen.

Basically, all the triblock copolymers that have been synthesized were categorized under three different groups, according to the variation of ε-CL and TMC ratio in the soft segment (B block). And under these three groups, there would be several triblock copolymers, which were the results of varying the molecular weight of the soft segment (B block) and the hard segment (A block). This allowed seeing what would be the effect of varying the molecular weight, the ratio of ε-CL and TMC, and the ratio between soft segment and hard segment.

Molecular Weights and Structural Properties

PLLA-P(CL-TMC)-PLLA with CL:TMC 50:50

TABLE 1

Molecular weight and molar ratio of various PLLA-P(CL-TMC)-PLLA with CL:TMC 50:50.

| A-B-A Target Mn (Da) | B block Mn (Da) | Total Mn (Da) | MWD | Target CL:TMC:LA (molar ratio) | $^1$H NMR CL:TMC:LA (molar ratio) |
|---|---|---|---|---|---|
| 5k-10k-5k | 10333 | 16468 | 1.63 | 1:1:1.50 | 1:0.94:1.26 |
| 10k-10k-10k | 10939 | 25257 | 1.39 | 1:1:3.00 | 1:0.95:2.77 |
| 5k-20k-5k | 20887 | 23737 | 1.51 | 1:1:0.75 | 1:0.92:0.53 |
| 10k-20k-10k | 20484 | 31151 | 1.57 | 1:1:1.50 | 1:0.94:1.27 |
| 5k-40k-5k | 32661 | 32948 | 1.44 | 1:1:0.38 | 1:0.92:0.21 |
| 10k-40k-10k | 34551 | 37777 | 1.48 | 1:1:0.75 | 1:0.91:0.58 |
| 20k-40k-20k | 34290 | 49161 | 1.22 | 1:1:1.50 | 1:0.83:1.35 |
| 40k-80k-40k | 30524 | 40868 | 1.41 | 1:1:1.50 | 1:0.96:1.24 |

Table 1 shows various triblock copolymers with the B block made of random copolymer of PCL and PTMC with molar ratio 50:50 and the A block made of PLLA. What has been varied here were the molecular weight of the middle block and the outer block. During the synthesis, before adding the L-lactide monomer, small amount of the polymer solution was taken for SEC characterization. It can be seen that for the B block of targeted molecular weight 10 kDa and 20 kDa the SEC results managed to reach the target, while for targeted 40 kDa the result was slightly lower, probably due to the presence of trace hydroxyl group-containing impurities in the reactants and reaction system which is getting more significant as the molecular weight increase.

Figure 2:
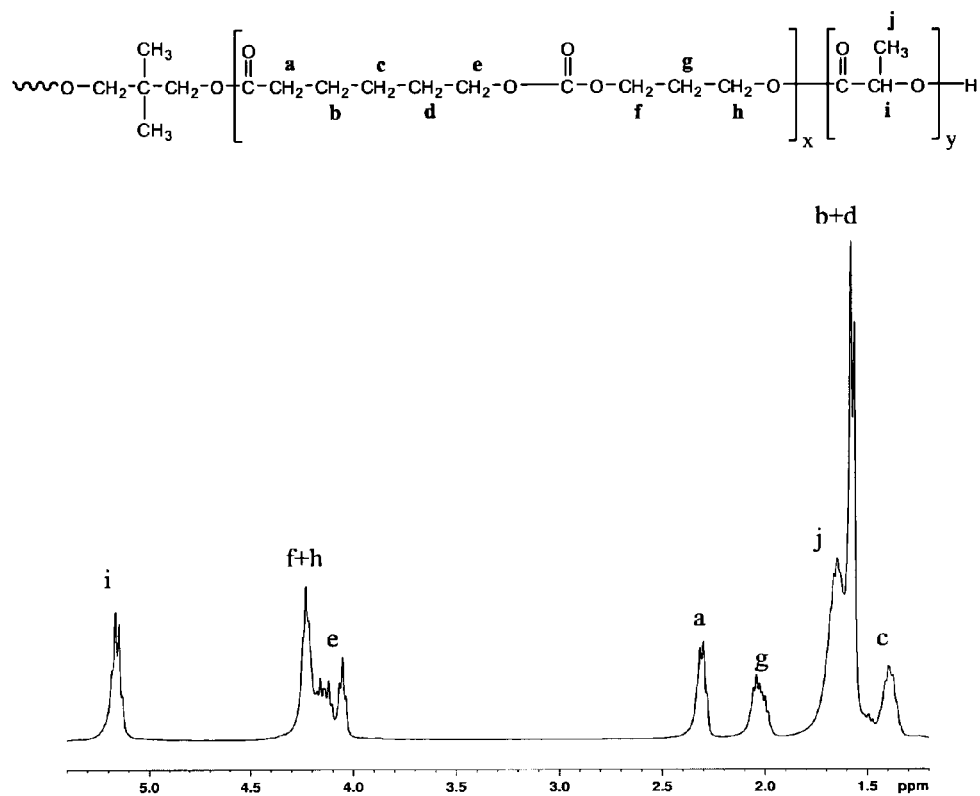
FIG. 2 illustrates the structure of one exemplary biodegradable thermoplastic elastomer and its $^1$H NMR spectrum (CL:TMC 50:50; 20k-40k-20k).

The typical $^1$H NMR spectrum of the triblock copolymer is shown in FIG. 2. The methylene protons from PCL: (a), (b+d), (c) and (e) are shown at 2.31, 1.66, 1.39, and 4.23 ppm respectively. Meanwhile, methylene protons from PTMC (f+h), and (g) are shown at 4.05 and 2.04 ppm, respectively. Also the methane (i) and methyl protons (j) of the PLLA block are shown at 5.16 and 1.64 ppm respectively. The peak splitting on the region of (f+h) and (e) peaks suggested randomization of PCL and PTMC. Monomer composition of the copolymer was determined from the integration ratio between proton signals (a), (g), and (i) (as the results are included in Table 1).

While the resulting CL and TMC composition ratio are very close to the target, the L-lactide contents of the purified triblock copolymers were lower than expected from the target composition as it can be seen from the $^1$H NMR result. This is due to the 90% to 95% conversion of L-lactide which might result from L-lactide transesterification during the polymerization. Nevertheless, the table shows that the composition and the block length of PLLA in the triblock copolymers can be well regulated.

PLLA-P(CL-TMC)-PLLA with CL:TMC 75:25

TABLE 2

Molecular weight and molar ratio of various PLLA-P(CL-TMC)-PLLA with CL:TMC 75:25.

| A-B-A Target Mn (Da) | B block Mn (Da) | Total Mn (Da) | Mw/Mn | Target CL:TMC:LA (molar ratio) | $^1$H NMR CL:TMC:LA (molar ratio) |
|---|---|---|---|---|---|
| 10k-40k-10k | 21373 | 31097 | 1.49 | 1:0.33:0.5 | 1:0.31:0.38 |
| 20k-40k-20k | 20328 | 41583 | 1.24 | 1:0.33:1 | 1:0.25:1.03 |
| 20k-80k-20k | 24537 | 35732 | 1.73 | 1:0.33:0.5 | 1:0.29:0.38 |
| 40k-80k-40k | 42437 | 56108 | 1.40 | 1:0.33:1 | 1:0.28:0.85 |

Table 2 shows four triblock copolymers with middle block of random copolymers between PCL and PTMC with CL:TMC molar ratio of 75:25. Similar to the previous section, it was observed that the resulting molecular weight fell below the target, especially for the middle block. Overall, the resulting molecular weights for the same targeted molecular weight were lower compared to those triblocks with CL:TMC 50:50, with 40k-80k-40k as an exception. Nevertheless, $^1$H NMR data also showed a good result for molar ratio of CL:TMC and a slightly lower L-lactide content than targeted.

Overall, the chemical shift of the triblock copolymers $^{13}$C NMR spectrum were similar to the spectrum from a tercopolymer of ε-CL, TMC, and PLLA from Jia et all (*Polymers for Advanced Technologies,* 2008, 19, (2), 159-166). It can be observed that the soft segment of the triblock copolymers with CL:TMC 75:25 was not as random as CL:TMC 50:50. For CL:TMC 50:50 the CO signal from either CL and TMC carbonyl atoms showed a dyad splitting of almost equal intensity. Meanwhile for CL:TMC 75:25, although the CO signal from CL carbonyl atom still showed a dyad splitting into peak (a) (CL-CL dyad) and peak (b) (CL-TMC dyad) (FIG. 2), the TMC carbonyl atom only showed TMC-TMC dyad, peak (g). From the L-lactide signals, it can be observed that there was indeed a certain amount of transesterification of the L-lactide block happened in the polymerization, showed by a cluster of small peaks (e), (f) located to the left of L-lactide-L-lactide dyad peak (d).

PLLA-P(CL-TMC)-PLLA with CL:TMC 90:10

TABLE 3

Molecular weight and molar ratio of various PLLA-P(CL-TMC)-PLLA with CL:TMC 90:10.

| A-B-A Target Mn (Da) | Mn (Da) | Mw (Da) | PDI | Target CL:TMC:LA (molar ratio) | $^1$H NMR CL:TMC:LA (molar ratio) |
|---|---|---|---|---|---|
| 20k-40k-20k | 50707 | 56504 | 1.11 | 1:0.11:0.83 | 1:0.11:0.7 |
| 40k-80k-40k | 100928 | 130251 | 1.29 | 1:0.11:0.83 | 1:0.09:0.74 |

In Table 3 the middle block of the triblock copolymers were random copolymer of PCL and PTMC with CL:TMC molar ratio of 90:10. The resulting molecular weight for 20k-40k-20k was more or less similar to CL:TMC 50:50 and CL:TMC 75:25, while for molecular weight 40k-80k-40k the GPC result showed a much higher value. This might show that for a higher targeted molecular weight, using less TMC inside the soft-block can improve the accuracy of resulting molecular weight, thus the conclusion that there are some incompatibility between CL and TMC monomer inside the polymerization. $^1$H NMR data showed a good result for molar ratio of CL:TMC and a slightly lower L-Lactide content than targeted.

Example 2

Thermal and Mechanical Properties of A-B-A Polymers

PLLA-P(CL-TMC)-PLLA with CL:TMC 50:50

TABLE 4

Thermal and mechanical properties of various PLLA-P(CL-TMC)-PLLA with CL:TMC 50:50.

| A-B-A Target Mn (Da) | Tg (° C.) | Tm (° C.) | ΔH (J/g) | Modulus (MPa) | Ultimate Tensile Strength (MPa) | Max Strain (%) |
|---|---|---|---|---|---|---|
| 5k-10k-5k | −40.8 | 140.7 | 21.41 | 8.3 | 2.6 | 29 |
| 10k-10k-10k | −38.6 | 158.6 | 36.03 | Too brittle | Too brittle | Too brittle |
| 5k-20k-5k | −41.8 | 125.4 | 6.9 | Too soft | Too soft | Too soft |
| 10k-20k-10k | −42.3 | 152.0 | 19.48 | 10.8 | 4.6 | 60 |
| 5k-40k-5k | −41.8 | 144.0 | 1.48 | Too soft | Too soft | Too soft |
| 10k-40k-10k | −41.9 | 133.4 | 3.55 | 3.5 | 1.5 | 74 |
| 20k-40k-20k | −48.8 | 151.0 | 15.56 | 12.5 | 4.5 | 520 |
| 40k-80k-40k | −45.6 | 159.2 | 20.56 | 13.3 | 3.3 | 278 |

Figure 3:
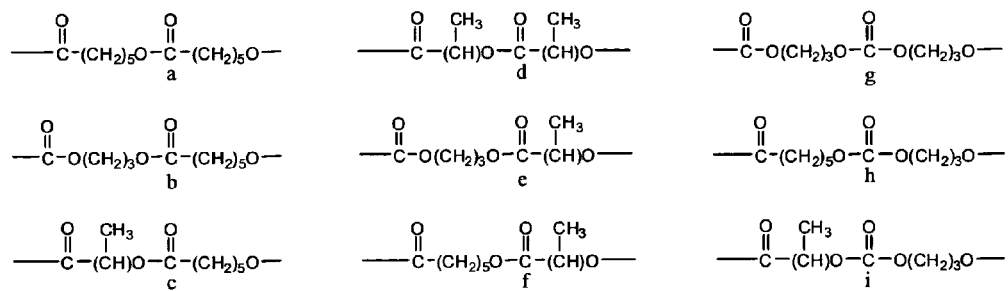
FIG. 3 illustrates a $^{13}$C NMR spectrum from region of carbonyl carbon atoms of CL:TMC 75:25 (20k-40k-20k) and their peaks assignment.
Figure 3:
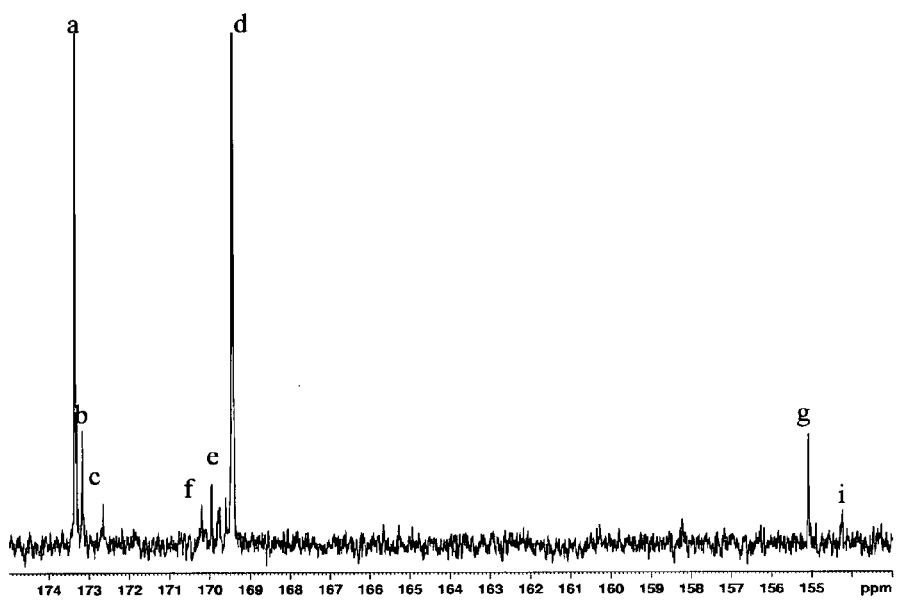

Preliminary study showed that random copolymer of PCL and PTMC with molar ratio of 50:50 was totally amorphous. So, it was expected that the triblock copolymer will have $T_m$ only from PLLA, FIG. 3 (a). Table 4 shows that the $T_m$ of the triblock copolymers ranged between 125° C. to 160° C. Since it was reported that for the homopolymer of PLLA the $T_m$ was around 175° C., it can be concluded that the middle block has the effect of lowering the $T_m$ of PLLA in the triblock. Meanwhile the $T_g$ of the triblock copolymers obviously came from the $T_g$ of random copolymer of PCL and PTMC. Since the $T_g$ of homopolymer of PCL and PTMC were −60° C. and −20° C. respectively, it was expected that the $T_g$ of the random copolymer lay between those two values which can be seen in table 4. Meanwhile the $T_g$ of the PLLA block were not observed.

Figure 4:
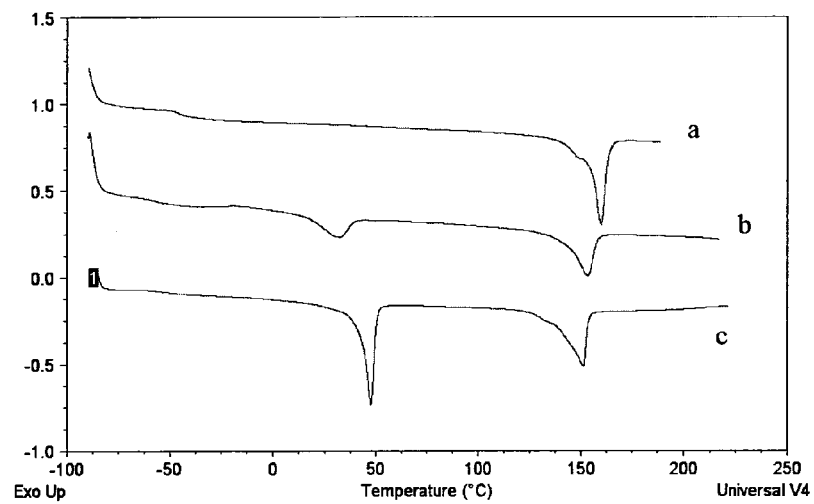
FIG. 4 illustrates a typical DSC result for triblock copolymer with middle block of: (a) CL:TMC 50:50, (b) CL:TMC 75:25, and (c) CL:TMC 90:10.
Figure 5:
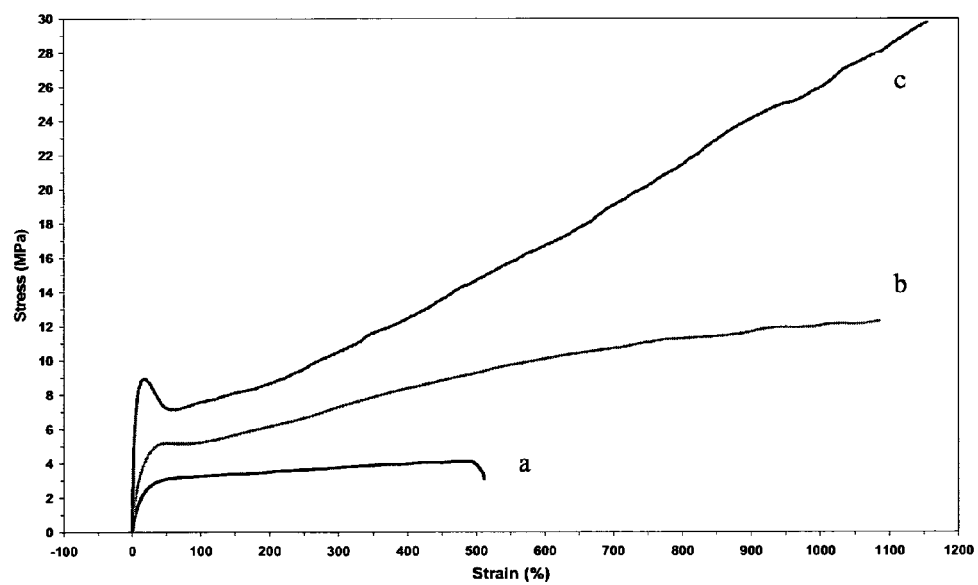
FIG. 5 illustrates stress strain measurements of a triblock copolymer: (a) CL:TMC 90:10, 40k-80k-40k; (b) CL:TMC 75:25, 40k-80k-40k; (c) CL:TMC 50:50, 40k-80k-40k.

Mechanical property wise, table 4 showed that molecular weight of the triblock copolymers and the length of L-lactide block played a big role. For triblock with targeted middle block of 10 kDa increasing the L-lactide content from 1.5 to 3 (with respect to CL content of 1) resulted in having a polymer which was too brittle to be made into a film. Meanwhile for middle block of 20 kDa, decreasing the L-lactide content from 1.5 to 0.75 (with respect to CL content of 1) gave rise to a polymer which was too soft to be made into a film. Comparing between those with same L-lactide content but different molecular weight, it was observed that increasing the molecular weight would result in increasing both the tensile strength and the maximum elongation of the triblock copolymers. From the table it can be seen that the triblock copolymers having molecular weight of 20k-40k-20k has a good mechanical properties with elongation up to 520%, FIG. 4 (a).

PLLA-P(CL-TMC)-PLLA with CL:TMC 75:25

TABLE 5

Thermal and mechanical properties of various PLLA-P(CL-TMC)-PLLA with CL:TMC 75:25.

| A-B-A Target Mn (Da) | Tg (° C.) | Tm (° C.) | ΔH (J/g) | Modulus (MPa) | Tensile Strength (MPa) | Max Strain (%) |
|---|---|---|---|---|---|---|
| 10k-40k-10k | −49.5 | 36.9 142.5 | 21.15 5.51 | 20 | 4.4 | 571 |
| 20k-40k-20k | −56.8 | 34.9 141.4 | 0.39 14.44 | 23.8 | 7.9 | 812 |
| 20k-80k-20k | −51.8 | 38.5 144.4 | 20.15 8.39 | 19.6 | 6.4 | 725 |
| 40k-80k-40k | −56.8 | 30.8 153.4 | 8.1 12.8 | 32 | 12.3 | 1084 |

Preliminary study showed that the random copolymer of PCL and PTMC with molar ratio 75:25 was a semi crystalline polymer with $T_g$ around −58° C. and $T_m$ around 30° C. So it was expected that the triblock copolymer had 2 $T_m$, one from the PCL-TMC block and other from the PLLA block, FIG. 4 (b). Again, table 5 shows that the middle block affected the $T_m$ of PLLA by lowering it from 175° C. ($T_m$ of pure PLLA) to around 140-150° C. Meanwhile, the $T_g$ from the middle block is significantly lower compared to the triblock with middle block of CL:TMC 50:50. This was expected as PCL has a lower $T_g$ compared to TMC. What was interesting from the DSC results was the crystallinity of the middle-block. Increasing the hard-block content from 10k-40k-10k to 20k-40k-20k will increase the crystallinity of hard-block (ΔH increased from 5.51 to 14.44 J/g), but somehow it will also decrease the crystallinity of the soft-block quite significantly (ΔH reduced from 21.15 to 0.39 J/g).

Looking at the mechanical properties, a significant improvement can be observed by increasing the molar ratio of CL:TMC 50:50 to 75:25 for all targeted molecular weight (compare table 4 and 5). All the triblock copolymers with soft-block of CL:TMC 75:25 managed to reach elongation beyond 500%. This result was surprising as previously it was believed that in order to have a good elongation and elasticity, the soft-block in thermoplastic elastomer has to be totally amorphous. Our data showed that triblock copolymer with targeted molecular weight 10k-40k-10k had a soft segment ΔH of 21.15 J/g, which translated into percentage crystallinity of as much as 23%, calculated using the heat of fusion ($\Delta H°_f$) of the total crystalline PLLA (93 J/g). Nevertheless, the triblock copolymers would still have 571% elongation while in the same time having a good the elastomeric behaviour. Meanwhile, the highest elongation of the triblock copolymers with soft segment CL:TMC 75:25 was from the targeted molecular weight of 40k-80k-40k, with an elongation of 1084%, FIG. 4 (b).

PLLA-(P(CL-TMC)-PLLA with CL:TMC 90:10

TABLE 6

Thermal and mechanical properties of various PLLA-P(CL-TMC)-PLLA with CL:TMC 90:10.

| A-B-A Target Mn (Da) | Tg (° C.) | Tm (° C.) | ΔH (J/g) | Modulus (MPa) | Tensile Strength (MPa) | Max Strain (%) |
|---|---|---|---|---|---|---|
| 20k-40k-20k | −55.6 | 47.5 151.2 | 25.15 19.9 | 72.3 | 9.42 | 67 |
| 40k-80k-40k | −60.7 | 49.5 159.4 | 16.7 18.2 | 56.8 | 29.5 | >1200 |

DSC results in table 6 show that for triblock copolymer with middle-block of CL:TMC 90:10, the $T_m$ of the soft-block are higher than those with middle-block of CL:TMC 75:25, so TMC actually had the effect of lowering the $T_m$ of PCL which was supposed to be 60° C. The crystallinity of the soft block are higher compared to middle-block CL:TMC 75:25 for the same targeted molecular weight triblock (compare table 6 and table 5). This proved the role of TMC in the middle-block as a disruptor for PCL crystallinity.

For the mechanical properties, the triblock copolymers with soft-block of CL:TMC 90:10 gave a very good elongation, very high modulus and tensile strength (table 6), although they lost their elasticity properties, marked by the appearance of yield point, FIG. 4(c). This showed that the crystallinity of the soft-block played an important role in the recovery properties of the triblock.

Example 3

Thermal and Mechanical Properties of A-B-A Polymers with Additives in Polymer A An extension of this work involved making the end-block (PLA) less crystalline and more extended by adding a comonomer. Results are shown below. From Tables 7 and 8 it can be seen that the addition of CL to LA improves the mechanical properties of the elastomer, such as max strain. In particular, there is an improvement in case the molecular ratio of CL in polymer B is >50%

TABLE 7

Molecular weight, molar ratio and thermal and mechanical properties of various PLLA-P(CL-TMC)-PLLA with CL:TMC 50:50 and additional CL in LLA.

| A-B-A Target Mn (Da) | Total Mn (Da) | PDI | Target CL:TMC:LA (molar ratio) | 1H NMR CL:TMC:LA (molar ratio) | Tg (° C.) | Tm (° C.) | ΔH (J/g) | Modulus (MPa) | Tensile Strength (MPa) | Max Strain (%) |
|---|---|---|---|---|---|---|---|---|---|---|
| 20k-40k-20k | 49161 | 1.22 | 1:1:1.50 | 1:0.83:1.35 | −48.8 | 151 | 15.6 | 12.5 | 4.5 | 520 |
| 20k-40k-20k (10% CL in LA) | 44463 | 1.34 | 1:0.87:1.17 | 1:0.74:1.10 | −48.4 | 138.5 | 11 | 10 | 4.7 | 914 |
| 20k-40k-20k (20% CL in LA) | 40077 | 1.49 | 1:0.77:0.92 | 1:0.79:0.81 | −44.7 | 138 | 11.8 | 9.1 | 2.5 | 300 |
| 20k-40k-20k (30% CL in LA) | 31419 | 1.44 | 1:0.69:0.72 | 1:0.80:0.75 | −39.2 | 111.5 | 1.3 | too soft | too soft | too soft |
| 40k-80k-40k | 40868 | 1.41 | 1:1:1.50 | 1:0.96:1.24 | −45.6 | 159.2 | 20.6 | 13.3 | 4.13 | 80 |
| 40k-80k-40k (10% CL in LA) | 39149 | 1.46 | 1:0.87:1.17 | 1:0.92:1.13 | −42.4 | 142.1 | 10.2 | 10 | 2.64 | 170 |
| 40k-80k-40k (30% CL in LA) | 30238 | 1.52 | 1:0.69:0.72 | 1:0.82:0.70 | −40.8 | 118.4 | 2.4 | too soft | too soft | too soft |

TABLE 8

Molecular weight, molar ratio and thermal and mechanical properties of various PLLA-P(CL-TMC)-PLLA with CL:TMC 75:25 and additional CL in LLA.

| A-B-A Target Mn (Da) | Total Mn (Da) | PDI | Target CL:TMC:LA (molar ratio) | 1H NMR CL:TMC:LA (molar ratio) | Tg (° C.) | Tm (° C.) | ΔH (J/g) | Modulus (MPa) | Tensile Strength (MPa) | Max Strain (%) |
|---|---|---|---|---|---|---|---|---|---|---|
| 0k-40k-20k | 41583 | 1.24 | 1:0.33:1 | 1:0.25:1.03 | −56.8 | 34.9 / 141.4 | 0.3 / 14.4 | 23.8 | 7.9 | 812 |
| 20k-40k-20k (10% CL in LA) | 43736 | 1.28 | 1:0.30:0.81 | 1:0.25:0.8 | −56.2 | 31.7 / 137.7 | 8 / 10.4 | 16 | 7.8 | 802 |
| 20k-40k-20k (20% CL in LA) | 45284 | 1.33 | 1:0.28:0.67 | 1:0.24:0.61 | −57.7 | 36.6 / 135.6 | 23 / 12.4 | 10.7 | >8.5 | >1200 |
| 20k-40k-20k (30% CL in LA) | 39499 | 1.54 | 1:0.26:0.54 | 1:0.29:0.5 | −57.6 | 36.3 / 130.1 | 14.5 / 7.6 | 6.6 | >7.3 | >1200 |
| 40k-80k-40k | 56108 | 1.4 | 1:0.33:1 | 1:0.28:0.85 | −56.8 | 30.8 / 153.4 | 8.1 / 12.8 | 32 | 12.3 | 1084 |
| 40k-80k-40k (10% CL in LA) | 50465 | 1.51 | 1:0.30:0.81 | 1:0.29:0.70 | −55.1 | 31.9 / 146.4 | 13.1 / 12.4 | 18 | 8 | 934 |
| 40k-80k-40k (30% CL in LA) | 40346 | 1.7 | 1:0.26:0.54 | 1:0.29:0.48 | −51.3 | 36 / 125.4 | 25.3 / 4.4 | 11.8 | >5.1 | >1200 |

The invention claimed is:

1. A biodegradable thermoplastic elastomer having the general formula

A-B-A wherein
each A is an amorphous polymer having a glass transition temperature (Tg)>40° C. or a semi-crystalline polymer having a glass transition temperature (Tg) and/or melting temperature (Tm)>40° C.;
wherein A comprises a polymer selected from the group consisting of poly(lactic acid) (PLA), poly-L-lactic acid (PLLA), poly-DL-lactic acid (PDLLA), poly(glycolic acid) (PGA), and poly(lactic-co-glycolic acid) (PLGA);
wherein A may further comprise poly(caprolactone) (PCL);
B is a copolymer of ε-caprolactone (CL) and at least one additional monomer selected from the group consisting of L-lactic acid (LLA), trimethyl carbonate (TMC), and glycolic acid (GA), or B is different to A and is poly (lactic-co-glycolic acid) (PLGA); and
wherein the molar ratio of CL to the at least one additional monomer in the copolymer B is in the range between about 1:0.09 to about 1:1.

2. The biodegradable thermoplastic elastomer of claim 1, wherein the elastomer does not contain 1,6-hexamethylene diisocyanate.

3. The biodegradable thermoplastic elastomer of claim 1, wherein the copolymer B is poly(caprolactone) (PCL):poly (trimethyl carbonate) (PTMC).

4. The biodegradable thermoplastic elastomer of claim 1, wherein A comprises poly(lactic acid).

5. The biodegradable thermoplastic elastomer of claim 4, wherein the PLA is a block polymer with a segment length of at least 10 units.

6. The biodegradable thermoplastic elastomer of claim 1, wherein A further comprises PCL in an amount of about 5 to about 35 wt.-%.

7. The biodegradable thermoplastic elastomer of claim 1, wherein the molar ratio of CL to the at least one additional monomer in the copolymer B is in the range between about 1:0.09 to about 1:0.99.

8. The biodegradable thermoplastic elastomer of claim 1, wherein the molar ratio of CL to the at least one additional monomer in the copolymer B is in the range between about 1:0.09 to about 1:0.5.

9. The biodegradable thermoplastic elastomer of claim 8, wherein the molar ratio of CL to the at least one additional monomer in the copolymer B is in the range between about 1:0.2 to 1:0.4.

10. The biodegradable thermoplastic elastomer of claim 1, wherein the crystallinity of B is <10%.

11. The biodegradable thermoplastic elastomer of claim 1, wherein the molecular weight of the biodegradable thermoplastic elastomer is at least about 35.000 u.

12. The biodegradable thermoplastic elastomer of claim 1, wherein the molecular weight of B is at least about 20.000 u.

13. The biodegradable thermoplastic elastomer of claim 1, wherein the molecular weight of each polymer A is at least about 10.000 u.

14. The biodegradable thermoplastic elastomer of claim 1, wherein the molecular weight of each A is about 10.000 u, about 20.000 u or about 40.000 u and the molecular weight of B is about 40.000 u or about 80.000 u.

15. The biodegradable thermoplastic elastomer of claim 1, wherein the overall molar ratio of CL:additional monomer: polymer A is between about 1:0.09:0.25 to about 1:0.99:1.35.

16. The biodegradable thermoplastic elastomer of claim 15, wherein the overall molar ratio of CL:additional monomer:polymer A is between about 1:0.2:0.5 and about 1:0.30: 0.85.

17. A medical device comprising a biodegradable thermoplastic elastomer of claim 1.

18. The medical device of claim 17, wherein the device is an implantable device selected from the group consisting of a stent, an occluder for patent foramen ovale (PFO) or atrial septal defect (ASD) or patent ductus arteriosus (pda), a scaffold for tissue engineering and implant applications.

19. The medical device of claim 18, wherein the stent is a fully-degradable stent for the coronary or peripheral arteries, for the trachea, biliary duct and ureter.

20. The medical device of claim 17, wherein the device is surgical suture material.

21. A packaging material comprising a biodegradable thermoplastic elastomer of claim 1.

22. The packaging material of claim 21, wherein the packaging material is selected from the group consisting of films, tape, cup, paper and cloth.

23. A method for the preparation of a biodegradable thermoplastic elastomer of claim 1 comprising:
   reacting a mixture of ε-caprolactone, at least one additional monomer, an initiator and tin-2-ethylhexanoate in an organic solvent in order to obtain copolymer B, wherein the at least one additional monomer is selected from the group consisting of L-lactic acid (LLA), trimethyl carbonate (TMC), glycolic acid (GA), and lactic-co-glycolic acid;
   adding monomer A, wherein the monomer A is selected from the group consisting of lactic acid (LA), L-lactic acid (LLA), DL-lactic acid (DLLA), glycolic acid (GA) and lactic-co-glycolic acid (LGA), wherein A may further comprise poly(caprolactone) (PCL);
   reacting the obtained mixture of copolymer B and monomer A; and
   precipitating the obtained polymer.

24. The method of claim 23, wherein the initiator is a diol.

25. The method of claim 24, wherein the diol is selected from ethylene glycol, 2,2-dimethyl-1,3-propandiol and butandiol.

26. The method of claim 23, wherein the organic solvent is selected from the group consisting of toluene, benzene and tetrahydrofuran.

27. The method of claim 23, wherein a solvent selected from the group consisting of methanol, ethanol, hexane and diethyl ether is added for precipitation.

28. The method of claim 23, wherein the mixture is refluxed for about 24 hours in order to obtain B.

29. The method of claim 23, wherein the mixture of B and monomer A is refluxed for about 24 hours.

30. The method of claim 23, wherein the molar ratio of CL:additional monomer is in the range between about 1:0.09 to about 1:0.99.

31. The method of claim 23, wherein the molar ratio of CL:additional monomer:monomer A is between about 1:0.09:0.25 to about 1:0.99:1.35.

* * * * *

UNITED STATES PATENT AND TRADEMARK OFFICE
CERTIFICATE OF CORRECTION

| | | |
|---|---|---|
| PATENT NO. | : 8,716,410 B2 | Page 1 of 1 |
| APPLICATION NO. | : 13/509566 | |
| DATED | : May 6, 2014 | |
| INVENTOR(S) | : Subramanian Venkatraman et al. | |

It is certified that error appears in the above-identified patent and that said Letters Patent is hereby corrected as shown below:

On the Title Page
Item (75):
"Subramanian Venkatraman, Singapore (SG); Marc Abadie, Singapore (SG); Leonardus Kresna Widjaja, Singapore (SG); Vitali Llpik, Singapore (SG)" should read, --Subramanian Venkatraman, Singapore (SG); Marc Abadie, Singapore (SG), Leonardus Kresna Widjaja, Singapore (SG); Vitali Lipik, Singapore (SG)--.

Signed and Sealed this
Thirtieth Day of September, 2014

Michelle K. Lee
*Deputy Director of the United States Patent and Trademark Office*